United States Patent
Matsushima et al.

(10) Patent No.: US 10,336,625 B2
(45) Date of Patent: Jul. 2, 2019

(54) ALUMINA SINTERED BODY AND BASE SUBSTRATE FOR OPTICAL DEVICE

(71) Applicant: NGK INSULATORS, LTD., Nagoya (JP)

(72) Inventors: Kiyoshi Matsushima, Nagoya (JP); Morimichi Watanabe, Nagoya (JP); Kei Sato, Tokai (JP); Tsutomu Nanataki, Toyoake (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 15/797,127

(22) Filed: Oct. 30, 2017

(65) Prior Publication Data

US 2018/0044195 A1    Feb. 15, 2018

Related U.S. Application Data

(63) Continuation of application No. PCT/JP2016/064096, filed on May 12, 2016.

(30) Foreign Application Priority Data

May 13, 2015  (JP) .................. 2015-098525
Jan. 25, 2016  (JP) .................. 2016-011190

(51) Int. Cl.
*C01F 7/00*  (2006.01)
*C01F 7/02*  (2006.01)
(Continued)

(52) U.S. Cl.
CPC ............... *C01F 7/02* (2013.01); *C01F 7/442* (2013.01); *C04B 35/115* (2013.01);
(Continued)

(58) Field of Classification Search
CPC . C04B 35/115; C04B 35/6342; C04B 35/632; C04B 35/6303; C04B 35/638;
(Continued)

(56) References Cited

U.S. PATENT DOCUMENTS 4,150,317 A    4/1979  Laska et al.
6,482,761 B1   11/2002 Watanabe et al.
(Continued)

FOREIGN PATENT DOCUMENTS

JP    S53-112912 A1    10/1978
JP    2001-064075 A1   3/2001
(Continued)

OTHER PUBLICATIONS

Hing, P., "The Influence of Some Processing Parameters on the Optical and Microstructural Properties of Sintered Aluminas," *Science of Ceramics*, 1976, vol. 8, pp. 159-172.
(Continued)

*Primary Examiner* — James A Fiorito
(74) *Attorney, Agent, or Firm* — Burr & Brown, PLLC

(57) ABSTRACT

An alumina sintered body according to the present invention includes a surface having a degree of c-plane orientation of 5% or more, the degree of c-plane orientation being determined by a Lotgering method using an X-ray diffraction profile obtained through X-ray irradiation at 2θ=20° to 70°. The alumina sintered body contains Mg and F, a Mg/F mass ratio is 0.05 to 3500, and a Mg content is 30 to 3500 ppm by mass. The alumina sintered body has a crystal grain size of 15 to 200 μm. When a field of view of 370.0 μm long×372.0 μm wide is photographed with a 1000-fold magnification and the photograph is visually observed, a number of pores having a diameter of 0.2 to 0.6 μm is 250 or less.

11 Claims, 7 Drawing Sheets

(51) Int. Cl.
| | |
|---|---|
| *C04B 35/115* | (2006.01) |
| *G01N 23/207* | (2018.01) |
| *G02B 1/02* | (2006.01) |
| *C01F 7/44* | (2006.01) |
| *C04B 35/632* | (2006.01) |
| *C04B 35/634* | (2006.01) |
| *C04B 35/645* | (2006.01) |

(52) U.S. Cl.
CPC ........ *C04B 35/632* (2013.01); *C04B 35/6342* (2013.01); *C04B 35/645* (2013.01); *G01N 23/207* (2013.01); *G02B 1/02* (2013.01); *C01P 2002/60* (2013.01); *C01P 2002/72* (2013.01); *C01P 2004/03* (2013.01); *C01P 2004/22* (2013.01); *C01P 2004/54* (2013.01); *C01P 2004/61* (2013.01); *C01P 2006/14* (2013.01); *C01P 2006/16* (2013.01); *C01P 2006/60* (2013.01); *C01P 2006/80* (2013.01); *C04B 2235/322* (2013.01); *C04B 2235/3206* (2013.01); *C04B 2235/3217* (2013.01); *C04B 2235/445* (2013.01); *C04B 2235/5292* (2013.01); *C04B 2235/5296* (2013.01); *C04B 2235/5436* (2013.01); *C04B 2235/5445* (2013.01); *C04B 2235/604* (2013.01); *C04B 2235/6025* (2013.01); *C04B 2235/658* (2013.01); *C04B 2235/6567* (2013.01); *C04B 2235/72* (2013.01); *C04B 2235/725* (2013.01); *C04B 2235/786* (2013.01); *C04B 2235/787* (2013.01); *C04B 2235/788* (2013.01)

(58) Field of Classification Search
CPC .......... C04B 35/6455; C04F 7/02; C04F 7/30; C30B 1/04; C30B 29/20; C30B 1/10
See application file for complete search history.

(56) References Cited

U.S. PATENT DOCUMENTS

| | | |
|---|---|---|
| 2006/0211568 A1 | 9/2006 | Wei |
| 2010/0248935 A1* | 9/2010 | Teratani .................. B32B 18/00 501/119 |
| 2011/0039685 A1 | 2/2011 | Mao et al. |
| 2011/0272734 A1 | 11/2011 | Hachigo et al. |

FOREIGN PATENT DOCUMENTS

| | | |
|---|---|---|
| JP | 2006-310272 A1 | 11/2006 |
| WO | 2010/082396 A1 | 7/2010 |

OTHER PUBLICATIONS

Yi, Hailan, et al., "Crystal Plane Evolution of Grain Oriented Alumina Ceramics with High Transparency," *Ceramics International*, 38 (2012), pp. 5557-5561.

International Search Report and Written Opinion (Application No. PCT/JP2016/064096) dated Jun. 7, 2016.

English translation of International Preliminary Report on Patentability (Chapter I) (Application No. PCT/JP2016/064096) dated Nov. 23, 2017, 9 pages.

* cited by examiner

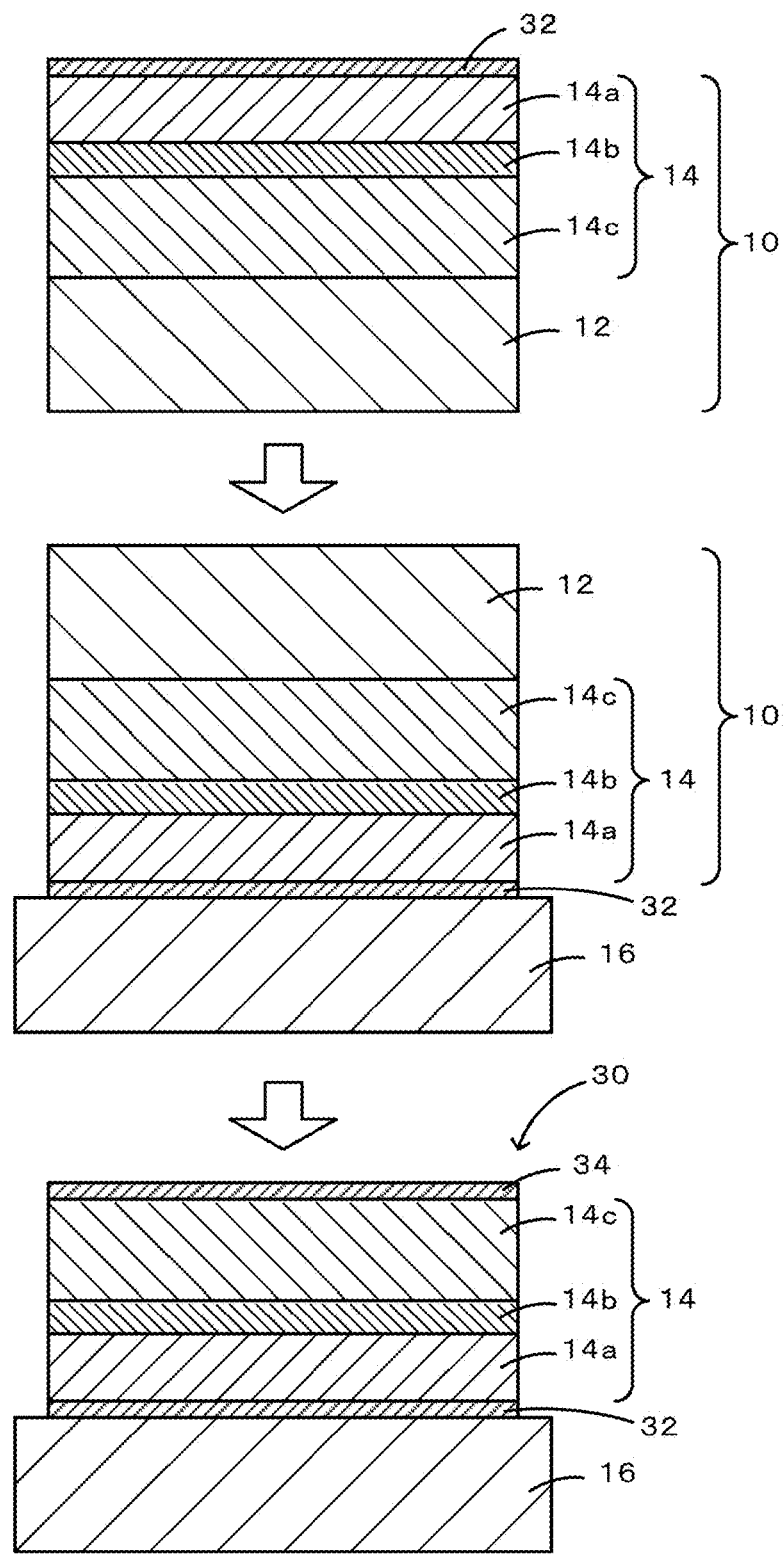

ALUMINA SINTERED BODY AND BASE SUBSTRATE FOR OPTICAL DEVICE

BACKGROUND OF THE INVENTION

1. Field of the Invention

The present invention relates to alumina sintered bodies and base substrates for optical devices.

2. Description of the Related Art

Transparent alumina sintered bodies have been known. For example, in NPL 1, an alumina suspension containing MgO is subjected to slip casting under a magnetic field and fired in a vacuum at 1850° C. for 5 hours to produce a transparent alumina sintered body with oriented grains. For example, an alumina sintered body produced under a magnetic field of 12 tesla has an in-line transmittance at 600 nm of 70.3% and a high degree of orientation of 97%. An alumina sintered body produced under a magnetic field of 8 tesla has an in-line transmittance at 600 nm of about 56% and a slightly high degree of orientation of 78%. Furthermore, the in-line transmittance and the degree of orientation decrease as the magnetic field strength decreases to 6 tesla and 4 tesla. The results conclude that the in-line transmittance and the degree of orientation increase as the magnetic field strength increases.

CITATION LIST

Non Patent Literature

NPL 1: Ceramics International 38 (2012) 5557-5561

SUMMARY OF THE INVENTION

In NPL 1, however, a sufficiently high degree of orientation is not achieved unless a high magnetic field of 12 tesla is applied, and thus an alumina sintered body having an in-line transmittance of 60% or more is not produced. An apparatus with which slip casting is performed while such a high magnetic field is applied is currently installed only in a limited number of facilities. Moreover, the produced sintered body includes many pores.

Accordingly, it is a main object of the present invention to provide an alumina sintered body including only a small number of pores and having high in-line transmittance.

An alumina sintered body according to the present invention includes a surface having a degree of c-plane orientation of 5% or more, the degree of c-plane orientation being determined by a Lotgering method using an X-ray diffraction profile obtained through X-ray irradiation at 2θ=20° to 70°. The alumina sintered body contains Mg and F, a Mg/F mass ratio is 0.05 to 3500, and a Mg content is 30 to 3500 ppm by mass. The alumina sintered body has a crystal grain size of 15 to 200 μm. When a field of view of 370.0 μm long×372.0 μm wide is photographed with a 1000-fold magnification and the photograph is visually observed, a number of pores having a diameter of 0.2 to 0.6 μm is 250 or less. A volume fraction of the pores having a diameter of 0.2 to 0.6 μm to the alumina sintered body is 130 ppm by volume or less. The alumina sintered body according to the present invention has, at a thickness of 0.5 mm, an in-line transmittance at 450 to 1000 nm of 60% or more and thus has high transparency. It has been believed so far that a high in-line transmittance is achieved only when the degree of orientation is high as in NPL 1. Nevertheless, according to the present invention, an alumina sintered body having a high in-line transmittance is produced when the degree of c-plane orientation is 5% or more. The reason why high transparency is achieved without such a high degree of c-plane orientation described in NPL 1 is unclear. It is believed that, for example, appropriate Mg and F contents, a large minimum crystal grain size of 15 μm, a small number of pores having a diameter of 0.2 to 0.6 μm, and a low volume fraction of pores having a diameter of 0.2 to 0.6 μm contribute to the high transparency in a combined manner.

A base substrate for an optical device according to the present invention is a substrate formed of the above alumina sintered body according to the present invention. Examples of the optical device include LEDs, LDs, solar cells, sensors, photodiodes, optical members, and window components.

BRIEF DESCRIPTION OF THE DRAWINGS

FIG. 4 includes schematic sectional views illustrating the production process of a vertical light-emitting device 30.

DETAILED DESCRIPTION OF THE INVENTION

Figure 1:
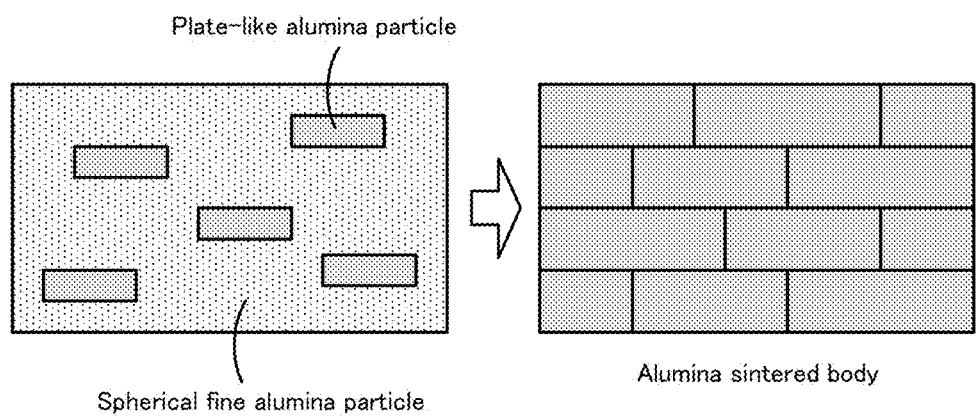
FIG. 1 schematically illustrates a process in which an alumina sintered body is produced by a TGG method.

Embodiments of the present invention will be described below. An alumina sintered body according to this embodiment includes a surface having a degree of c-plane orientation of 5% or more, the degree of c-plane orientation being determined by a Lotgering method using an X-ray diffraction profile obtained through X-ray irradiation at 2θ=20° to 70°. The alumina sintered body contains Mg and F, the Mg/F mass ratio is 0.05 to 3500, and the Mg content is 30 to 3500 ppm by mass. The alumina sintered body has a crystal grain size of 15 to 200 μm. When a field of view of 370.0 μm long×372.0 μm wide is photographed with a 1000-fold magnification and the photograph is visually observed, the number of pores having a diameter of 0.2 to 0.6 μm is 250 or less. The volume fraction of the pores having a diameter of 0.2 to 0.6 μm to the alumina sintered body is 130 ppm by volume or less.

The degree of c-plane orientation is calculated using an XRD apparatus (e.g., RINT-TTR III manufactured by Rigaku Corporation) as follows. A particular cross section (e.g., a cross section parallel to a c-plane) of an alumina sintered body is smoothed by polishing. Then, the cross section is irradiated with X-rays to obtain an X-ray diffraction profile at 2θ=20° to 70°. The degree of c-plane orientation is calculated from formula below using the X-ray diffraction profile. The c-plane is a (006) plane of alumina. In the formula, P is a value obtained from XRD of the alumina sintered body according to this embodiment, and $P_0$ is a value calculated from standard α-alumina (JCPDS card No. 46-1212). The alumina sintered body according to this embodiment is a highly-oriented alumina sintered body having a degree of c-plane orientation of 5% or more.

$$\text{Degree of } c\text{-plane orientation } [\%] = \frac{p - p_0}{1 - p_e} \times 100 \quad [\text{Math. 1}]$$

$$p_0 = \frac{I_0(006)}{\sum I_0(hkl)}$$

$$p = \frac{I_z(006)}{\sum I_s(hkl)}$$

The Mg content is determined by inductively coupled plasma (ICP) emission spectrometry and the F content is determined by dynamic secondary ion mass spectrometry (D-SIMS). The Mg/F mass ratio is preferably 0.05 to 3500, more preferably 0.1 to 10, and further preferably 0.2 to 3.5. The Mg content is preferably 30 to 3500 ppm by mass, more preferably 100 to 2000 ppm by mass, and further preferably 100 to 1500 ppm by mass. Mg is added in the form of, for example, MgO, $MgF_2$, or $MgNO_3$. When the Mg content and the F content are within the above ranges, a high in-line transmittance can be achieved. From the viewpoint of increasing the in-line transmittance, the contents of impurity elements other than Mg, C, and F are each preferably 50 ppm or less and more preferably 10 ppm or less. The C content is preferably 100 ppm or less, more preferably 70 ppm or less, and further preferably 50 ppm or less. For example, the C content and the S content can be determined by firing (high-frequency heating)-infrared absorption spectroscopy, the N content can be determined by an inert gas fusion-thermal conductivity method, and the H content can be determined by inert gas fusion-nondispersive infrared absorption spectroscopy. The contents of other elements (mainly Si, Fe, Ti, Na, Ca, K, P, V, Cr, Mn, Co, Ni, Cu, Zn, Y, Zr, Pb, Bi, Li, Be, B, Cl, Sc, Ga, Ge, As, Se, Br, Rb, Sr, Nb, Mo, Ru, Rh, Pd, Ag, Cd, In, Sn, Sb, Te, Cs, Ba, Hf, Ta, W, Ir, Pt, Au, Hg, La, Ce, Pr, Nd, Sm, Eu, Gd, Tb, Dy, Ho, Er, Tm, Yb, and Lu) can be determined by ICP emission spectrometry or ICP mass spectrometry. From the viewpoint of bending strength of a sintered body, the F content is preferably as low as possible and is preferably 200 ppm by mass or less.

The crystal grain size is an average size of sintered grains and is preferably 15 to 200 μm, more preferably 20 to 200 μm, more preferably 20 to 150 μm, and further preferably 20 to 100 μm. The crystal grain size is determined as follows. A particular cross section (e.g., a cross section parallel to a c-plane) of an alumina sintered body is mirror-polished and subjected to thermal etching treatment. Then, the cross section is imaged. In the obtained image, a rectangular field of view is set and two diagonal lines are drawn in the rectangular field of view. The length of a line segment inside each grain that intersects the diagonal lines is determined. A value obtained by multiplying the average of the lengths by 1.5 is defined as the crystal grain size.

The number of pores having a diameter of 0.2 to 0.6 μm is counted as follows. That is, a freely selected cross section of the alumina sintered body according to this embodiment is polished by ion milling. The polished cross section is observed using a scanning electron microscope with a 1000-fold magnification, and the number of pores is counted. For example, a field of view of 92.5 μm long×124.0 μm wide on the polished cross section is photographed using a scanning electron microscope with a 1000-fold magnification to obtain 12 continuous photographs in four rows by three columns (370.0 μm long×372.0 μm wide). The number of pores in the 12 photographs is visually counted. The photographs may be secondary electron images or backscattered electron images. Regardless of secondary electron images and backscattered electron images, the alumina appears gray and the pores appear black or a darker gray than alumina. The polishing is performed by ion milling because grains are not separated from the cross section. A polishing machine for the ion milling is, for example, a cross section polisher manufactured by JEOL Ltd. In the photograph magnified by 1000 times, the pores appear as black spots and thus the pores can be sufficiently recognized through visual inspection. The number of pores having a diameter of 0.2 to 0.6 μm is preferably 250 or less, more preferably 50 or less, further preferably 40 or less, further preferably 15 or less, and particularly preferably 3 or less. The in-line transmittance tends to increase as the number of pores decreases. The volume fraction of the pores having a diameter of 0.2 to 0.6 μm to the alumina sintered body is preferably 130 ppm or less, more preferably 25 ppm or less, further preferably 15 ppm or less, further preferably 10 ppm or less, and particularly preferably 2 ppm or less. The in-line transmittance tends to increase as the volume fraction of the pores decreases. To further increase the in-line transmittance, both the number of pores and the volume fraction need to be decreased. The combination of the number of pores and the volume fraction is preferably 250 or less and 130 ppm or less, more preferably 50 or less and 25 ppm or less, further preferably 40 or less and 15 ppm or less, further preferably 15 or less and 10 ppm or less, and particularly preferably 3 or less and 2 ppm or less.

The number of pores having a diameter of 1 μm or more is counted as follows. That is, a freely selected cross section of the alumina sintered body according to this embodiment is polished by ion milling. The polished cross section is then observed using a scanning electron microscope with a 500-fold magnification, and the number of pores is counted. For example, a field of view of 223.4 μm long×321.4 μm wide on the polished cross section is photographed using a scanning electron microscope with a 500-fold magnification to obtain 30 continuous photographs in six rows by five columns (1340.4 μm long×1607.0 μm wide). The number of pores in the 30 photographs is visually counted. The polishing is performed by ion milling because grains are not separated from the cross section. A polishing machine for the ion milling is, for example, a cross section polisher manufactured by JEOL Ltd. In the photograph magnified by 500 times, the pores appear as black spots and thus the pores can be sufficiently recognized through visual inspection. The number of pores having a diameter of 1 μm or more is preferably 50 or less. The in-line transmittance tends to increase as the number of pores decreases.

The number of foreign substances contained in the alumina sintered body according to this embodiment is preferably as small as possible. When a field of view of 370.0 μm long×372.0 μm wide is photographed with a 1000-fold magnification, the number of visually observed foreign substances having a diameter of 0.2 to 0.6 μm is preferably 50 or less and more preferably 40 or less. The in-line transmittance tends to increase as the number of foreign substances decreases. The foreign substance is a substance different from alumina. For example, when the polished cross section is photographed using a scanning electron microscope, the foreign substance can be easily distinguished from the surrounding alumina because of different contrast levels. Specifically, the contrast between alumina and the foreign substance is often distinguishable regardless of secondary electron images and backscattered electron images, but the foreign substance can be more easily distinguished from the alumina by observing the cross section as a backscattered electron image. The number of foreign substances is counted by the following method. A freely selected cross section of the alumina sintered body according to this embodiment is polished by ion milling. The polished cross section is then observed as a backscattered electron image using a scanning electron microscope with a 1000-fold magnification, and the number of foreign substances is counted. For example, a field of view of 92.5 μm long×124.0 μm wide on the polished cross section is photographed using a scanning electron microscope with a 1000-fold magnification to obtain 12 continuous photographs in four rows by three columns (370.0 μm long×372.0 μm wide). The number of foreign substances in the 12 photographs is visually counted. The foreign substances can be more precisely distinguished by a combination of a scanning electron microscope and an energy dispersive X-ray spectroscopy (EDS) or an electron probe microanalyzer (EPMA).

In the alumina sintered body according to this embodiment, a sample obtained from the alumina sintered body and having a thickness of 0.5 mm preferably has an in-line transmittance of 60% or more at a wavelength of 450 to 1000 nm. The in-line transmittance can be determined using a spectrophotometer (e.g., Lambda 900 manufactured by Perkin Elmer). Herein, when the thickness of the sample is converted to the thickness of the others, the following conversion formula may be used. The formula is cited from Scripta Materialia vol. 69, pp 362-365 (2013). In the formula, T1 is an actually measured in-line transmittance, T2 is a converted in-line transmittance, t1 is an actually measured thickness, t2 is a converted thickness, and R is surface reflection (0.14 for alumina) derived from a material.

$$T2=(1-R)(T1/(1-R))^{(t2/t1)}$$

The present inventors have found that the transparency is improved by decreasing the inclination (tilt angle) of the crystallographic axis of each alumina grain relative to the orientation angle (e.g., c axis) of the alumina sintered body. The tilt angle can be evaluated using an X-ray rocking curve full width at half maximum (XRC·FWHM) obtained by measuring the surface of a transparent alumina sintered body by an X-ray rocking curve method (omega scan). From the viewpoint of transparency, the tilt angle is preferably as small as possible. The XRC·FWHM is preferably 15° or less, more preferably 100 or less, further preferably 7.50 or less, particularly preferably 50 or less, much more preferably 40 or less, and still more preferably 10 or less.

The alumina sintered body according to this embodiment can be used as a base substrate for forming films of, for example, GaN, ZnO, AlN, SiC, and InN. The surface of the alumina sintered body according to this embodiment is preferably polished before film formation. This eliminates the irregularities on the surface, which makes it easy to form a film and suppresses formation of defects on the film.

The alumina sintered body according to this embodiment can be produced by, for example, forming and sintering a mixed powder containing a plate-like alumina powder and a fine alumina powder whose average grain size is smaller than the plate-like alumina powder. By forming the mixed powder containing the plate-like alumina powder and the fine alumina powder, the plate-like grains are easily oriented during the forming (e.g., tape casting, extrusion, pouring, injection molding, and uniaxial pressing). Furthermore, the plate-like alumina powder serves as a seed crystal (template) and the fine alumina powder serves as a matrix during sintering, and the template undergoes homoepitaxial growth while taking in the matrix. This production method is referred to as a TGG (templated grain growth) method. FIG. 1 schematically illustrates a process in which an alumina sintered body is produced by a TGG method. In the TGG method, the microstructure of an alumina sintered body to be obtained can be controlled by adjusting the grain size and mixing ratio of the plate-like alumina powder and the fine alumina powder. Thus, the densification is easily performed and the degree of orientation is easily improved compared with the case where the plate-like alumina powder alone is sintered.

The alumina sintered body according to this embodiment is obtained by subjecting a compact to pressure sintering (e.g., hot-press sintering and HIP sintering). Before the pressure sintering, pressureless presintering may be performed. In the case of HIP sintering, a capsule method may be employed. The sintering temperature is preferably 1800° C. to 2050° C. The pressure in the case of hot-press sintering is preferably 50 kgf/cm$^2$ or more and more preferably 200 kgf/cm$^2$ or more. The pressure in the case of HIP sintering is preferably 1000 kgf/cm$^2$ or more and more preferably 2000 kgf/cm$^2$ or more. The content of the plate-like alumina powder in the mixed powder is preferably 0.1 to 15 mass % and more preferably 0.5 to 10 mass %.

A base substrate for optical devices is a substrate formed of the above-described alumina sintered body according to this embodiment. Examples of the optical devices include light-emitting devices and light-receiving devices. For example, when a GaN layer is formed on the base substrate for optical devices, the base substrate for optical devices can be used as a light-emitting substrate for large and low-cost LEDs and the like compared with the case where a sapphire is used for a base substrate. Since the base substrate for optical devices is transparent, the substrate can be separated by laser lift-off. Furthermore, when the base substrate is not separated, light can be extracted through the base substrate. Instead of the GaN layer, for example, a ZnO layer, an AlN layer, or an InN layer may be formed.

Figure 2:
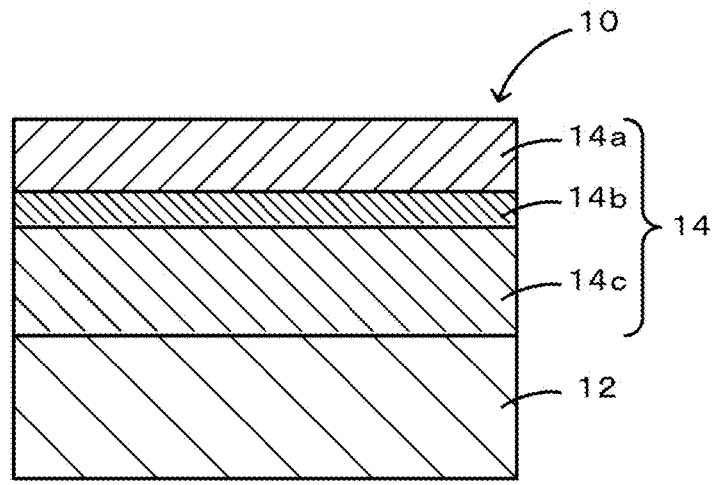
FIG. 2 is a schematic sectional view illustrating a light-emitting device 10.

Examples of using the base substrate for optical device as a light-emitting device will be described below. As illustrated in FIG. 2, a light-emitting device 10 includes a base substrate 12 and a light-emitting functional layer 14 formed on the base substrate 12. The light-emitting functional layer 14 is configured to emit light upon voltage application on the basis of the light-emitting principle of LEDs. Herein, an n-type layer 14c, an active layer 14b, and a p-type layer 14a are stacked in this order from the base substrate 12. The light-emitting functional layer 14 is formed of, for example, a GaN-based material, a ZnO-based material, or an AlN-based material.

Figure 3:
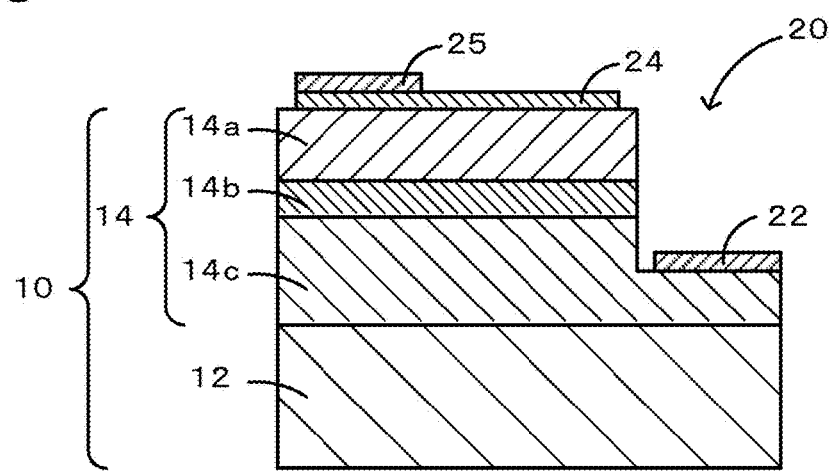
FIG. 3 is a schematic sectional view illustrating a horizontal light-emitting device 20.

As illustrated in FIG. 3, in a horizontal light-emitting device 20, the n-type layer 14c is formed so as to have a stepped surface in a peripheral portion of the light-emitting functional layer 14 in the light-emitting device 10. A cathode electrode 22 is disposed on the stepped surface of the n-type layer 14c, and an anode electrode pad 25 is disposed above the surface of the p-type layer 14a with an optically translucent anode electrode 24. In this horizontal light-emitting device 20, an electric current flows not only in a direction of the normal to the light-emitting functional layer 14, but also in a horizontal direction.

As illustrated in FIG. 4, in a vertical light-emitting device 30, a cathode electrode 34 is disposed on the surface of the n-type layer 14c of the light-emitting functional layer 14, and a mounting substrate 16 is attached to the surface of the p-type layer 14a with an anode electrode 32 disposed therebetween. The vertical light-emitting device 30 is produced by forming an anode electrode 32 on the surface of the p-type layer 14a of the light-emitting device 10, joining the anode electrode 32 to a mounting substrate 16, removing the base substrate 12 by laser lift-off, and forming a cathode electrode 34 on the exposed surface of the n-type layer 14c. In this vertical light-emitting device 30, an electric current flows in a direction of the normal to the light-emitting functional layer 14. Laser lift-off is used in this manner because the base substrate 12 has high optical translucency due to its high in-line transmittance.

EXAMPLES

Experimental Example 1

Figure 5A:
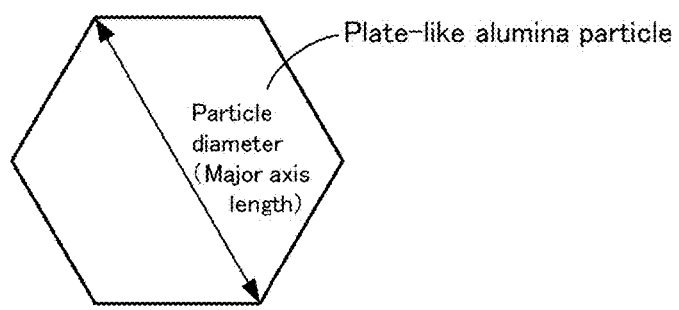
FIG. 5A is a plan view schematically illustrating a plate-like alumina particle and FIG. 5B is a front view schematically illustrating the plate-like alumina particle.
Figure 5B:
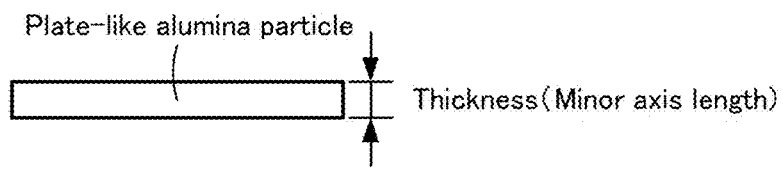

1. Production of Alumina Sintered Body
(1) Preparation of Plate-like Alumina Powder In a pot mill, 96 parts by mass of a high-purity γ-alumina powder (TM-300D, manufactured by TAIMEI CHEMICALS CO., LTD.), 4 parts by mass of a high-purity $AlF_3$ powder (special grade, manufactured by KANTO CHEMICAL CO., INC.), and 0.17 parts by mass of a high-purity α-alumina powder (TM-DAR, manufactured by TAIMEI CHEMICALS CO., LTD., D50=1 µm) serving as a seed crystal were mixed with each other for 5 hours using IPA (isopropyl alcohol) as a solvent and ϕ2 mm alumina balls. After the mixing in the pot mill, the IPA was dried using an evaporator to obtain a mixed powder. Into a high-purity alumina sagger (volume 750 $cm^3$) having a purity of 99.5 mass %, 300 g of the obtained mixed powder was inserted and a high-purity alumina lid having a purity of 99.5 mass % was put thereon. The mixed powder was heat-treated in an electric furnace with air flow at 900° C. for 3 hours. The air flow rate was 25000 cc/min. The heat-treated powder was annealed in the air at 1150° C. for 42.5 hours, and then pulverized for 4 hours using ϕ2 mm alumina balls to obtain a plate-like alumina powder having an average grain size of 2 µm, a thickness of 0.3 µm, and an aspect ratio of about 7. The average grain size, average thickness, and aspect ratio of the grains were determined by observing freely selected 100 grains in the plate-like alumina powder using a scanning electron microscope (SEM). The average grain size is an average of major axis lengths of grain plate surfaces. The average thickness is an average of minor axis lengths (thicknesses) of grains. The aspect ratio is given as an average grain size/average thickness. FIG. 5A is a plan view schematically illustrating a plate-like alumina particle and FIG. 5B is a front view schematically illustrating the plate-like alumina particle. The plate-like alumina particle has a substantially hexagonal shape when viewed in plan. The grain size of the plate-like alumina particle is as illustrated in FIG. 5A, and the thickness of the plate-like alumina particle is as illustrated in FIG. 5B.

(2) Tape Casting

One point five parts by mass of the plate-like alumina powder prepared in (1) and 98.5 parts by mass of a fine alumina powder (TM-DAR, average grain size 0.1 µm, manufactured by TAIMEI CHEMICALS CO., LTD.) having an average grain size smaller than the thickness of the plate-like alumina powder were mixed with each other. To 100 parts by mass of the mixed alumina powder, 0.025 parts by mass of magnesium oxide (500A, manufactured by Ube Material Industries, Ltd.), 7.8 parts by mass of polyvinyl butyral (product number: BM-2, manufactured by SEKISUI CHEMICAL CO., LTD.) serving as a binder, 3.9 parts by mass of di(2-ethylhexyl) phthalate (manufactured by Kurogane Kasei Co., Ltd.) serving as a plasticizer, 2 parts by mass of sorbitan trioleate (RHEODOL SP-O30, manufactured by Kao Corporation) serving as a dispersant, and 2-ethylhexanol serving as a dispersion medium were added and mixed with each other. The amount of the dispersion medium was adjusted such that the slurry viscosity was 20000 cP. The thus-prepared slurry was formed into a sheet shape on a PET film by a doctor blade method such that the thickness after drying was 20 µm. The obtained tape was cut into a circular shape having a diameter of 50.8 mm (2 inches). Then, 150 sheets of the tape were stacked on top of each other and placed on an Al plate having a thickness of 10 mm. Then, the tape was inserted into a package and subjected to vacuum packing. The vacuum-packed product was subjected to isostatic pressing in hot water at 85° C. at a pressure of 100 $kgf/cm^2$ to obtain a disc-shaped compact.

(3) Sintering

Figure 6:
FIG. 6 is a photograph illustrating an external appearance of a sample of an alumina sintered body.

The obtained compact was placed in a degreasing furnace and degreased at 600° C. for 10 hours. The degreased compact was subjected to hot-press sintering using a graphite mold in a nitrogen atmosphere at 1975° C. for 4 hours at a surface pressure of 200 $kgf/cm^2$, and then cooled. When the temperature reached 1200° C., the surface pressure was released to obtain an alumina sintered body having a diameter of 50.8 mm. FIG. 6 is a photograph illustrating an external appearance of a sample of the obtained alumina sintered body (after mirror polishing with 2 µm diamond abrasive grains). The NGK logo in FIG. 6 is the registered trademark of NGK INSULATORS, LTD.

(4) Surface Polishing

The both sides of the plate surface of the obtained alumina sintered body were mirror-polished with diamond abrasive grains so that the alumina sintered body had a thickness of 0.5 mm. The polished sintered body (sample) was washed with acetone, ethanol, and ion-exchanged water in this order for 10 minutes each to obtain a sample for analyzing the degree of c-plane orientation, the in-line transmittance, and the D-SIMS.

2. Properties of Alumina Sintered Body
(1) Calculation of Degree of c-Plane Orientation To check the degree of orientation of the obtained alumina sintered body, the degree of c-plane orientation was measured by XRD. The polished surface of the mirror-polished alumina sintered body was irradiated with X-rays using an XRD apparatus (RINT-TTR III manufactured by Rigaku Corporation) to measure an XRD profile at 2θ=20° to 70°. Specifically, the measurement was performed using CuKα rays at a voltage of 50 kV at a current of 300 mA. The degree of c-plane orientation was calculated by a Lotgering method. Specifically, the degree of c-plane orientation was calculated from the above-mentioned formula. The alumina sintered body of Experimental Example 1 had a degree of c-plane orientation of 96.1%.

(2) Tilt Angle

Figure 7:
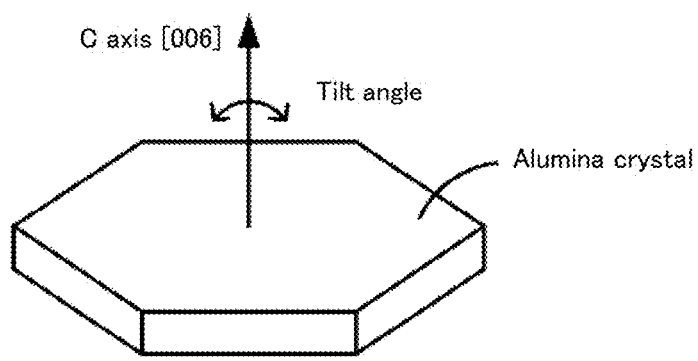
FIG. 7 is an explanatory view for describing a tilt angle.
Figure 8:
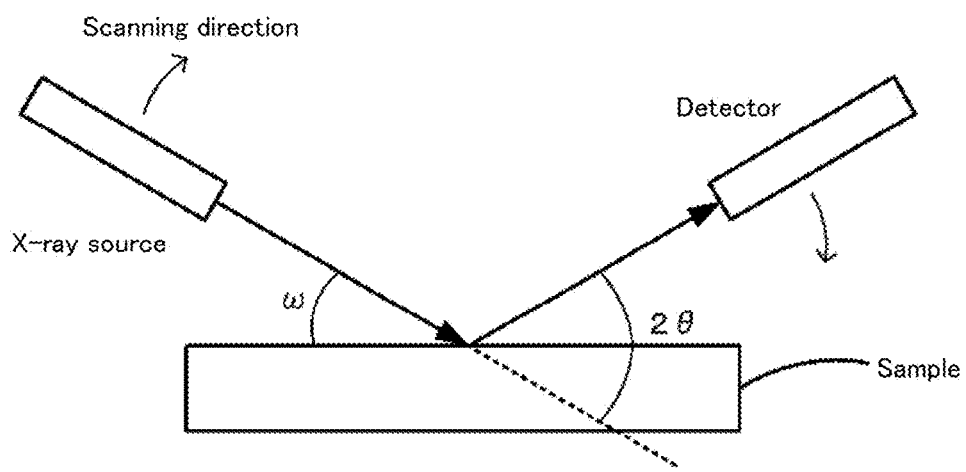
FIG. 8 is an explanatory view for describing rocking curve measurement.

The tilt angle indicates the inclination distribution of a crystallographic axis and is a parameter for evaluating how frequently the crystal orientation of alumina is inclined from the c-axis. FIG. 7 is a schematic explanatory view for describing the tilt angle. Herein, the tilt angle is expressed as an X-ray rocking curve (XRC) full width at half maximum (FWHM). The XRC·FWHM was determined by scanning the plate surface (the same surface as that in the measurement of the degree of c-plane orientation) of the alumina sintered body while interlocking an X-ray source and a detector as illustrated in FIG. 8 and calculating the full width at half maximum of the obtained curve. This measurement method in which 2θ (an angle between a detector and incident X-rays) is fixed at the diffraction peak position and only ω (an angle between a sample substrate surface and incident X-rays) is scanned is referred to as a rocking curve measurement. The apparatus was a RINT-TTR III manufactured by Rigaku Corporation. The measurement was performed using CuKα rays at a voltage of 50 kV at a current of 300 mA. The scanning range of ω was set to 3.8° to 38.8°. The XRC-FWHM of the alumina sintered body of Experimental Example 1 was 4.5°.

(3) Purity (3-1) Elements Other than Al, O, and F

The alumina sintered body was pulverized with an alumina mortar having a purity of 99.9%, and then elements other than Al, O, and F were quantitatively analyzed by the following method. For the elements other than Al, O, and F of the alumina sintered body in Experimental Example 1, 112 ppm of Mg and 40 ppm of C were detected, and elements other than Mg and C were not detected.

C and S were analyzed by firing (high-frequency heating)-infrared absorption spectroscopy using a carbon/sulfur analyzer (CS844 manufactured by LECO). The detection limit was 10 ppm.

N was analyzed by an inert gas fusion-thermal conductivity method using an oxygen/nitrogen analyzer (EMGA-650W manufactured by HORIBA, Ltd.). The detection limit was 10 ppm.

H was analyzed by inert gas fusion-nondispersive infrared absorption spectroscopy using a hydrogen analyzer (EMGA-921 manufactured by HORIBA, Ltd.). The detection limit was 10 ppm.

Elements (mainly Si, Fe, Ti, Na, Ca, Mg, K, P, V, Cr, Mn, Co, Ni, Cu, Zn, Y, Zr, Pb, Bi, Li, Be, B, Cl, Sc, Ga, Ge, As, Se, Br, Rb, Sr, Nb, Mo, Ru, Rh, Pd, Ag, Cd, In, Sn, Sb, Te, Cs, Ba, Hf, Ta, W, Ir, Pt, Au, Hg, La, Ce, Pr, Nd, Sm, Eu, Gd, Tb, Dy, Ho, Er, Tm, Yb, and Lu) other than the above elements were analyzed by dissolving an alumina powder by sulfuric acid decomposition under pressure conforming to JIS R 1649 and by using an inductively coupled plasma (ICP) emission spectrometer (PS3520UV-DD manufactured by Hitachi High-Tech Science Corporation). The detection limit was 10 ppm.

Ba, Sr, and Pb were separately analyzed by the following method, but were not detected.

Ba, Sr, and Pb were analyzed by melting an alumina powder with a sodium carbonate melt and using an inductively coupled plasma (ICP) mass spectrometer (iCAPQC manufactured by Thermo Fisher Scientific K.K.).

(3-2) F

The mirror-polished alumina sintered body was subjected to dynamic secondary ion mass spectrometry (D-SIMS). The measurement apparatus was ADEPT 1010 manufactured by PHI. The measurement conditions were as follows.

Primary ion species: $Cs^+$
Primary ion acceleration energy: 3 keV
Secondary ion polarity: Negative
Charge compensation: E-gun
Sputtering cycle: 100 to 500 cycles The average between the 200th sputtering cycle and the 300th sputtering cycle was defined as a F content. In the quantitative analysis, an analytical sample and a standard sample having the same composition (AlO) as the analytical sample and having a known concentration were measured under the same conditions to determine a relative sensitivity coefficient. Consequently, the F content in the sintered body was 59 ppm.

(3-3) Mg/F

The Mg content (ppm by mass) determined in (3-1) was divided by the F content (ppm by mass) determined in (3-2) to determine Mg/F. The Mg/F in Experimental Example 1 was 1.9.

(4) Pore and Foreign Substance

Figure 9:
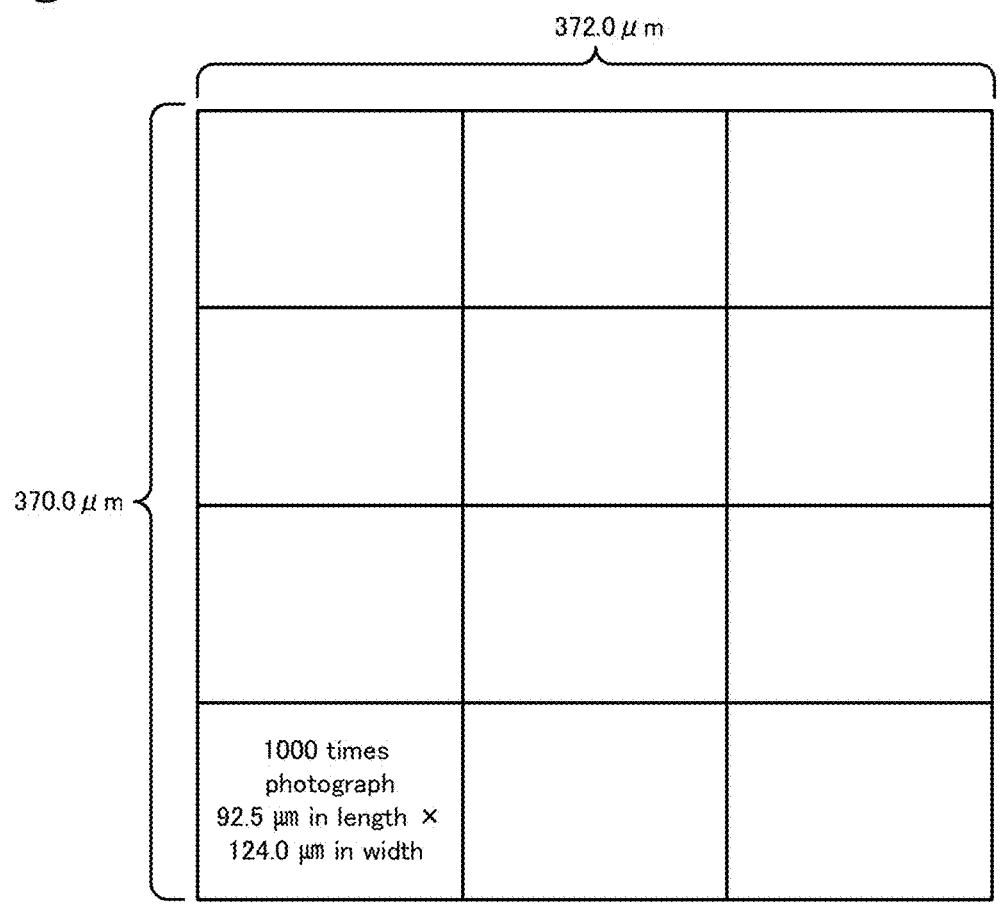
FIG. 9 is an explanatory view illustrating a state in which high-magnification photographs are continuously arranged.

A freely selected cross section of the obtained alumina sintered body was subjected to preliminary polishing with diamond abrasive grains, and then polished using a cross section polisher (CP) (IB-09010CP manufactured by JEOL Ltd.). The CP belongs to the category of ion milling. The CP was used because grains are not separated from the polished surface. The obtained cross section was photographed with a scanning electron microscope (JSM-6390 manufactured by JEOL Ltd.). Specifically, a field of view of 92.5 μm long×124.0 μm wide was photographed with a 1000-fold magnification. The photographs were arranged in four rows by three columns as illustrated in FIG. 9 to obtain continuous photographs (370.0 μm long×372.0 μm wide) of secondary electron images and backscattered electron images. The number of pores having a diameter of 0.2 to 0.6 μm and the number of foreign substances having a diameter of 0.2 to 0.6 μm were counted through visual inspection. Herein, the longest side of the observed pores was defined as a diameter. In the photographs of secondary electron images and backscattered electron images, the alumina appears gray, the pores appear black, and the foreign substances appear in tones with contrast levels different from those of the alumina and the pores. Therefore, the alumina, the pores, and the foreign substances can be easily distinguished through visual inspection. In portions where the alumina, the pores, and the foreign substances were not easily distinguished, they were distinguished by using an EDS (JSM-6390 manufactured JEOL Ltd.). The average of the longest sides of the observed pores and foreign substances was defined as a diameter. Furthermore, the volume fraction of the pores having a diameter of 0.2 to 0.6 μm to the alumina sintered body was calculated using the following formula.

$$\text{Pore volume fraction} = \{\pi \times (R/2)^2 / 137640\} \times N$$

R: Diameter of pores (μm)
N: Number of pores

The average diameter of pores having a diameter of 0.2 to 0.6 μm in the alumina sintered body of Experimental Example 1 was 0.32 μm. The number of the pores was 9. The number of foreign substances was 6. The volume fraction of the pores having a diameter of 0.2 to 0.6 μm to the alumina sintered body was 5.3 ppm by volume.

Figure 10:
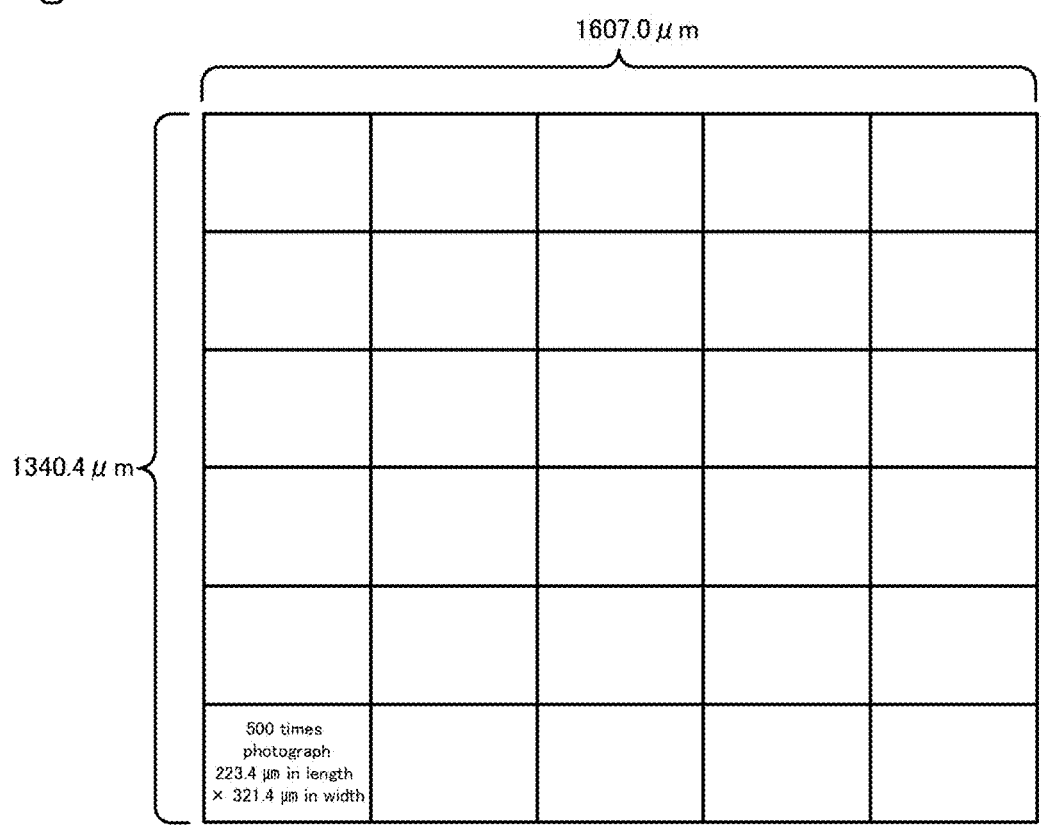
FIG. 10 is an explanatory view illustrating a state in which high-magnification photographs are continuously arranged.

In addition to the pores having a diameter of 0.2 to 0.6 μm, the number of pores having a diameter of 1 μm or more was counted as follows. That is, a freely selected cross section of the obtained alumina sintered body was subjected to preliminary polishing with diamond abrasive grains, and then polished using the CP mentioned above. The obtained cross section was photographed with the scanning electron microscope mentioned above. Specifically, a field of view of 223.4 μm long×321.4 μm wide was photographed with a 500-fold magnification. The photographs were arranged in six rows by five columns as illustrated in FIG. 10 to obtain continuous photographs (1340.4 μm long×1607.0 μm wide). The number of pores having a diameter of 1 μm or more was counted through visual inspection. Herein, the longest side of the observed pores was defined as a diameter. Since the pores and portions other than the pores have a distinct contrast, they can be easily distinguished through visual inspection. The number of the pores in the alumina sintered body of Experimental Example 1 was zero.

(5) Crystal Grain Size

The mirror-polished alumina sintered body was inserted into a high-purity alumina sagger (volume 750 cm³) having a purity of 99.5 mass % and subjected to thermal etching treatment in the air at 1550° C. for 45 minutes. As a result of the thermal etching treatment, the grain boundaries can be clearly observed because the etching rate is different between the inside of grains and the grain boundary portions. The surface subjected to the thermal etching treatment was photographed using a scanning electron microscope (JSM-6390 manufactured by JEOL Ltd.). The range of a field of view was set as follows. That is, when a rectangle was placed on the obtained image and its diagonal lines were drawn, the size of the rectangle was adjusted so that each of the diagonal lines intersected 10 to 30 grains. The rectangle was defined as the range of a field of view. The length of the line segment inside each grain that intersected the two diagonal lines of the rectangle was determined. A value obtained by multiplying the average of the lengths by 1.5 was defined as an average grain size of the plate surface. The average grain size (crystal grain size) in Experimental Example 1 was 63 µm.

(6) In-Line Transmittance

The in-line transmittance of the mirror-polished alumina sintered body was measured at a wavelength of 450 to 1000 nm using a spectrophotometer (Lambda 900 manufactured by Perkin Elmer). The in-line transmittance in Experimental Example 1 was 80.6% or more.

(7) Four-Point Bending Strength

A rod with a size of 4×0.5×20 mm was cut out from the mirror-polished alumina sintered body, and the four-point bending strength was measured. The distance between external supporting points was set to 15 mm, and the distance between the internal supporting points was set to 5 mm. The four-point bending strength was calculated from the formula of the four-point bending strength described in JIS 1601: 2008 using a load at which a test piece was broken.

Experimental Example 2

An alumina sintered body was produced in the same manner as in Experimental Example 1, except that the sintering temperature in the sintering in 1. (3) was changed to 1900° C. in the production of the alumina sintered body. The properties in 2. (1) to (7) were also determined for the produced alumina sintered body. Table 1 shows the results.

Experimental Example 3

An alumina sintered body was produced in the same manner as in Experimental Example 1, except that 0.75 parts by mass of the plate-like alumina powder and 99.25 parts by mass of the fine alumina powder were mixed in the tape casting in 1. (2) and the sintering temperature in 1. (3) was changed to 1900° C. in the production of the alumina sintered body. The properties in 2. (1) to (7) were also determined for the produced alumina sintered body. Table 1 shows the results.

Experimental Example 4

An alumina sintered body was produced in the same manner as in Experimental Example 1, except that the amount of magnesium oxide added was changed to 0.05 parts by mass in the tape casting in 1. (2) and the sintering temperature in 1. (3) was changed to 1900° C. in the production of the alumina sintered body. The properties in 2. (1) to (7) were also determined for the produced alumina sintered body. Table 1 shows the results.

Experimental Example 5

An alumina sintered body was produced in the same manner as in Experimental Example 1, except that 2.0 parts by mass of the plate-like alumina powder and 98.0 parts by mass of the fine alumina powder were mixed and the amount of magnesium oxide added was changed to 0.035 parts by mass in the tape casting in 1. (2), and the sintering temperature in 1. (3) was changed to 1900° C. in the production of the alumina sintered body. The properties in 2. (1) to (7) were also determined for the produced alumina sintered body. Table 1 shows the results.

Experimental Example 6

An alumina sintered body was produced in the same manner as in Experimental Example 1, except that 2.5 parts by mass of the plate-like alumina powder and 97.5 parts by mass of the fine alumina powder were mixed and the amount of magnesium oxide added was changed to 0.035 parts by mass in the tape casting in 1. (2), and the sintering temperature in 1. (3) was changed to 1950° C. in the production of the alumina sintered body. The properties in 2. (1) to (7) were also determined for the produced alumina sintered body. Table 1 shows the results.

Experimental Example 7

An alumina sintered body was produced in the same manner as in Experimental Example 1, except that 2.0 parts by mass of the plate-like alumina powder and 98.0 parts by mass of the fine alumina powder were mixed and the amount of magnesium oxide added was changed to 0.035 parts by mass in the tape casting in 1. (2), and the sintering temperature in 1. (3) was changed to 1850° C. in the production of the alumina sintered body. The properties in 2. (1) to (7) were also determined for the produced alumina sintered body. Table 1 shows the results.

Experimental Example 8

An alumina sintered body was produced in the same manner as in Experimental Example 1, except that 2.5 parts by mass of the plate-like alumina powder and 97.5 parts by mass of the fine alumina powder were mixed in the tape casting in 1. (2) and the sintering temperature in 1. (3) was changed to 1850° C. in the production of the alumina sintered body. The properties in 2. (1) to (7) were also determined for the produced alumina sintered body. Table 1 shows the results.

Experimental Example 9

An alumina sintered body was produced in the same manner as in Experimental Example 1, except that the annealing treatment was not performed in the preparation of the plate-like alumina powder in 1. (1), 5.0 parts by mass of the plate-like alumina powder and 95.0 parts by mass of the fine alumina powder were mixed and the amount of magnesium oxide added was changed to 0.25 parts by mass in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results.

Experimental Example 10

An alumina sintered body was produced in the same manner as in Experimental Example 1, except that the annealing treatment was not performed in the preparation of the plate-like alumina powder in 1. (1), 5.0 parts by mass of the plate-like alumina powder and 95.0 parts by mass of the fine alumina powder were mixed and the amount of magnesium oxide added was changed to 0.1 parts by mass in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results.

Experimental Example 11

An alumina sintered body was produced in the same manner as in Experimental Example 1, except that the annealing treatment was not performed in the preparation of the plate-like alumina powder in 1. (1), 5.0 parts by mass of the plate-like alumina powder and 95.0 parts by mass of the fine alumina powder were mixed in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results.

Experimental Example 12

An alumina sintered body was produced in the same manner as in Experimental Example 1, except that the annealing treatment was not performed in the preparation of the plate-like alumina powder in 1. (1), 10.0 parts by mass of the plate-like alumina powder and 90.0 parts by mass of the fine alumina powder were mixed and the amount of magnesium oxide added was changed to 0.25 parts by mass in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results. The XRC-FWHM was not measured because no peak appeared in the rocking curve measurement.

Experimental Example 13

An alumina sintered body was produced in the same manner as in Experimental Example 1, except that the annealing treatment was performed at 900° C. for 3 hours in the preparation of the plate-like alumina powder in 1. (1), 2.5 parts by mass of the plate-like alumina powder and 97.5 parts by mass of the fine alumina powder were mixed in the tape casting in 1. (2), and the sintering temperature in 1. (3) was changed to 1950° C. in the production of the alumina sintered body. The properties in 2. (1) to (7) were also determined for the produced alumina sintered body. Table 1 shows the results.

Experimental Example 14

An alumina sintered body was produced in the same manner as in Experimental Example 1, except that the annealing treatment was performed at 900° C. for 3 hours in the preparation of the plate-like alumina powder in 1. (1), 2.5 parts by mass of the plate-like alumina powder and 97.5 parts by mass of the fine alumina powder were mixed in the tape casting in 1. (2), and the sintering temperature in 1. (3) was changed to 1900° C. in the production of the alumina sintered body. The properties in 2. (1) to (7) were also determined for the produced alumina sintered body. Table 1 shows the results.

Experimental Example 15

An alumina sintered body was produced in the same manner as in Experimental Example 1, except that 2.0 parts by mass of the plate-like alumina powder and 98.0 parts by mass of the fine alumina powder were mixed and the amount of magnesium oxide added was changed to 0.035 parts by mass in the tape casting in 1. (2) in the production of the alumina sintered body. The properties in 2. (1) to (7) were also determined for the produced alumina sintered body. Table 1 shows the results.

Experimental Example 16

An alumina sintered body was produced in the same manner as in Experimental Example 1, except that the annealing treatment was not performed in the preparation of the plate-like alumina powder in 1. (1), 2.5 parts by mass of the plate-like alumina powder and 97.5 parts by mass of the fine alumina powder were mixed and the amount of magnesium oxide added was changed to 0.05 parts by mass in the tape casting in 1. (2), and the sintering temperature in 1. (3) was changed to 1850° C. in the production of the alumina sintered body. The properties in 2. (1) to (7) were also determined for the produced alumina sintered body. Table 1 shows the results.

Experimental Example 17

An alumina sintered body was produced in the same manner as in Experimental Example 1, except that, in the tape casting in 1. (2), AKP-20 (average grain size 0.5 µm, manufactured by Sumitomo Chemical Company, Limited) was used as the fine alumina powder, 2.0 parts by mass of the plate-like alumina powder and 98.0 parts by mass of the fine alumina powder were mixed, and the amount of magnesium oxide added was changed to 0.035 parts by mass in the production of the alumina sintered body. The properties in 2. (1) to (7) were also determined for the produced alumina sintered body. Table 1 shows the results.

Experimental Example 18

An alumina sintered body was produced in the same manner as in Experimental Example 1, except that the annealing treatment was performed at 1150° C. for 42.5 hours and then the pulverization was performed using ϕ2 mm alumina balls for 50 hours to obtain a plate-like alumina powder having an average grain size of 1 µm, a thickness of 0.3 µm, and an aspect ratio of about 3 in the preparation of the plate-like alumina powder in 1. (1); 2.0 parts by mass of the plate-like alumina powder and 98.0 parts by mass of the fine alumina powder were mixed and the amount of magnesium oxide added was changed to 0.035 parts by mass in the tape casting in 1. (2); and the sintering temperature in 1. (3) was changed to 1800° C. in the production of the alumina sintered body. The properties in 2. (1) to (7) were also determined for the produced alumina sintered body. Table 1 shows the results.

Experimental Example 19

An alumina sintered body was produced in the same manner as in Experimental Example 1, except that the annealing treatment was not performed in the preparation of the plate-like alumina powder in 1. (1), 2.5 parts by mass of the plate-like alumina powder and 97.5 parts by mass of the fine alumina powder were mixed and the amount of magnesium oxide added was changed to 0.05 parts by mass in the tape casting in 1. (2), and the sintering temperature in 1. (3) was changed to 1990° C. in the production of the alumina sintered body. The properties in 2. (1) to (7) were also determined for the produced alumina sintered body. Table 1 shows the results.

Experimental Example 20

An alumina sintered body was produced in the same manner as in Experimental Example 1, except that the sintering temperature in 1. (3) was changed to 1750° C. in the production of the alumina sintered body. The properties in 2. (1) to (7) were also determined for the produced alumina sintered body. Table 1 shows the results.

Experimental Example 21

An alumina sintered body was produced in the same manner as in Experimental Example 1, except that the annealing treatment was not performed in the preparation of the plate-like alumina powder in 1. (1), 2.5 parts by mass of the plate-like alumina powder and 97.5 parts by mass of the fine alumina powder were mixed and the amount of magnesium oxide added was changed to 0.02 parts by mass in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results.

Experimental Example 22

An alumina sintered body was produced in the same manner as in Experimental Example 1, except that only the fine alumina powder was used without using the plate-like alumina powder in the tape casting in 1. (2) in the production of the alumina sintered body. The properties in 2. (1) to (7) were also determined for the produced alumina sintered body. Table 1 shows the results.

Experimental Example 23

An alumina sintered body was produced in the same manner as in Experimental Example 1, except that the annealing treatment was performed at 900° C. for 1 hour in the preparation of the plate-like alumina powder in 1. (1), 30.0 parts by mass of the plate-like alumina powder and 70.0 parts by mass of the fine alumina powder were mixed in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results.

Experimental Example 24

An alumina sintered body was produced in the same manner as in Experimental Example 1, except that the annealing treatment was performed at 1250° C. for 12 hours in the preparation of the plate-like alumina powder in 1. (1), and 0.5 parts by mass of the plate-like alumina powder and 99.5 parts by mass of the fine alumina powder were mixed and the amount of magnesium oxide added was changed to 0.7 parts by mass in the tape casting in 1. (2) in the production of the alumina sintered body. The properties in 2. (1) to (7) were also determined for the produced alumina sintered body. Table 1 shows the results.

Experimental Example 25

An alumina sintered body was produced in the same manner as in Experimental Example 1, except that 0.5 parts by mass of the plate-like alumina powder and 99.5 parts by mass of the fine alumina powder were mixed and the amount of magnesium oxide added was changed to 0.007 parts by mass in the tape casting in 1. (2), and the sintering temperature in 1. (3) was changed to 2000° C. in the production of the alumina sintered body. The properties in 2. (1) to (7) were also determined for the produced alumina sintered body. Table 1 shows the results. In this Experimental Example, many abnormal grain growth portions were observed and cracks were formed on the outer periphery of abnormal grains.

Experimental Example 26

An alumina sintered body was produced in the same manner as in Experimental Example 1, except that 2.0 parts by mass of the plate-like alumina powder and 98.0 parts by mass of the fine alumina powder were mixed and the amount of magnesium oxide added was changed to 0.035 parts by mass in the tape casting in 1. (2), and the sintering temperature in 1. (3) was changed to 1600° C. in the production of the alumina sintered body. The properties in 2. (1) to (7) were also determined for the produced alumina sintered body. Table 1 shows the results.

Experimental Example 27

An alumina sintered body was produced in the same manner as in Experimental Example 1, except that 0.5 parts by mass of the plate-like alumina powder and 99.5 parts by mass of the fine alumina powder were mixed and the amount of magnesium oxide added was changed to 1.0 part by mass in the tape casting in 1. (2), and the sintering temperature in 1. (3) was changed to 1800° C. in the production of the alumina sintered body. The properties in 2. (1) to (7) were also determined for the produced alumina sintered body. Table 1 shows the results.

Experimental Example 28

An alumina sintered body was produced in the same manner as in Experimental Example 1, except that 0.5 parts by mass of the plate-like alumina powder and 99.5 parts by mass of the fine alumina powder were mixed and the amount of magnesium oxide added was changed to 0.003 parts by mass in the tape casting in 1. (2), and the sintering temperature in 1. (3) was changed to 1700° C. in the production of the alumina sintered body. The properties in 2. (1) to (7) were also determined for the produced alumina sintered body. Table 1 shows the results.

TABLE 1

| Experimental examples | Annealing in preparation of the powder (° C., hr) | Mixed alumina powder - Plate-like alumina (parts by mass) | Mixed alumina powder - Fine alumina (parts by mass) | Amount of MgO (parts by mass) | Sintering temperature (° C.) | Alumina sintered body - Degree of orientation (%) | XRC·FWHM (°) | Mg content (ppm) | F content (ppm) | Mg/F | Pore of φ0.2-0.6 μm - Number | Pore of φ0.2-0.6 μm - Average diameter (μm) | Pore of φ0.2-0.6 μm - Volume fraction (volppm) | Number of pores of φ1 μm or more | Number of foreign substances | Impurity content | Crystal grain size (μm) | In-line transmittance (%) | Four-point bending strength (MPa) |
|---|---|---|---|---|---|---|---|---|---|---|---|---|---|---|---|---|---|---|---|
| 1 | 1150, 42.5 | 1.5 | 98.5 | 0.025 | 1975 | 96.1 | 4.5 | 112 | 59 | 1.9 | 9 | 0.32 | 5.3 | 0 | 6 | ND*2 | 63 | ≥80.6 | 461 |
| 2 | 1150, 42.5 | 1.5 | 98.5 | 0.025 | 1900 | 67.7 | 6.6 | 113 | 71 | 1.6 | 34 | 0.28 | 15.2 | 8 | 11 | ND*2 | 38 | ≥74.6 | 488 |
| 3 | 1150, 42.5 | 0.75 | 99.25 | 0.025 | 1900 | 93.4 | 6.1 | 113 | 36 | 3.1 | 31 | 0.24 | 10.2 | 2 | 19 | ND*2 | 34 | ≥76.6 | 636 |
| 4 | 1150, 42.5 | 1.5 | 98.5 | 0.05 | 1900 | 95.1 | 6.8 | 224 | 71 | 3.2 | 60 | 0.31 | 32.9 | 4 | 37 | ND*2 | 37 | ≥62.9 | 506 |
| 5 | 1150, 42.5 | 2 | 98 | 0.035 | 1900 | 99.9 | 5.9 | 157 | 90 | 1.7 | 22 | 0.30 | 11.3 | 6 | 9 | ND*2 | 38 | ≥76.6 | 492 |
| 6 | 1150, 42.5 | 2.5 | 97.5 | 0.035 | 1950 | 97.5 | 6.8 | 158 | 91 | 1.7 | 21 | 0.28 | 9.4 | 11 | 14 | ND*2 | 46 | ≥78.3 | 484 |
| 7 | 1150, 42.5 | 2 | 98 | 0.035 | 1850 | 71 | 9.3 | 157 | 95 | 1.7 | 61 | 0.27 | 25.4 | 12 | 20 | ND*2 | 26 | ≥65.1 | 518 |
| 8 | 1150, 42.5 | 2.5 | 97.5 | 0.025 | 1850 | 99.7 | 6.4 | 112 | 120 | 0.9 | 42 | 0.28 | 18.6 | 6 | 21 | ND*2 | 89 | ≥71.9 | 356 |
| 9 | 1150, 42.5 | 5 | 95 | 0.25 | 1800 | 99.8 | 4.9 | 1119 | 660 | 1.7 | 12 | 0.31 | 6.6 | 2 | 10 | ND*2 | 30 | ≥79.9 | 281 |
| 10 | —, — | 5 | 95 | 0.1 | 1800 | 76 | 7.1 | 447 | 660 | 0.7 | 24 | 0.27 | 10.0 | 3 | 17 | ND*2 | 92 | ≥77.5 | 152 |
| 11 | —, — | 5 | 95 | 0.025 | 1800 | 55.5 | 12.1 | 113 | 660 | 0.2 | 48 | 0.29 | 23.0 | 7 | 31 | ND*2 | 22 | ≥69.5 | 271 |
| 12 | —, — | 10 | 90 | 0.25 | 1800 | 5.9 | —*1 | 1214 | 1320 | 0.9 | 44 | 0.29 | 21.1 | 2 | 24 | ND*2 | 67 | ≥70.9 | 280 |
| 13 | 900, 3 | 2.5 | 97.5 | 0.025 | 1950 | 100 | 4.8 | 111 | 146 | 0.8 | 13 | 0.25 | 4.6 | 0 | 3 | ND*2 | 48 | ≥80.8 | 440 |
| 14 | 900, 3 | 2.5 | 97.5 | 0.025 | 1900 | 99.9 | 6.3 | 112 | 170 | 0.7 | 34 | 0.26 | 13.1 | 17 | 9 | ND*2 | 46 | ≥74.8 | 431 |
| 15 | 1150, 42.5 | 2 | 98 | 0.035 | 1975 | 100 | 3.7 | 157 | 89 | 1.8 | 2 | 0.23 | 0.6 | 0 | 2 | ND*2 | 55 | ≥84.8 | 438 |
| 16 | —, — | 2.5 | 97.5 | 0.05 | 1850 | 99.9 | 3.5 | 222 | 243 | 0.9 | 2 | 0.23 | 0.6 | 0 | 3 | ND*2 | 30 | ≥84.6 | 288 |
| 17 | 1150, 42.5 | 2 | 98 | 0.035 | 1975 | 99.8 | 4.8 | 156 | 131 | 1.2 | 3 | 0.31 | 1.6 | 0 | 10 | Si:28 | 60 | ≥84.1 | 439 |
| 18 | 1150, 42.5 | 2 | 98 | 0.035 | 1800 | 95.6 | 7.1 | 158 | 91 | 1.7 | 42 | 0.28 | 18.8 | 0 | 7 | ND*2 | 16 | ≥71.8 | 552 |
| 19 | —, — | 2.5 | 97.5 | 0.05 | 1990 | 5.6 | —*1 | 224 | 212 | 1.1 | 6 | 0.28 | 2.7 | 0 | 3 | ND*2 | 192 | ≥82.8 | 106 |
| 20 | 1150, 42.5 | 1.5 | 98.5 | 0.025 | 1750 | 17.4 | —*1 | 113 | 96 | 1.2 | 243 | 0.20 | 55 | 10 | 28 | ND*2 | 28 | ≥80.9 | 465 |
| 21 | 1150, 42.5 | 2.5 | 97.5 | 0.02 | 1800 | 6.5 | —*1 | 90 | 251 | 0.4 | 60 | 0.60 | 123.3 | 14 | 11 | ND*2 | 130 | ≥60.8 | 125 |
| 22 | —, — | 0 | 100 | 0.025 | 1975 | 0.0 | —*1 | 112 | 0 | — | 14 | 0.26 | 5.4 | 5 | 4 | ND*2 | 102 | ≥46.2 | 382 |
| 23 | 900, 1 | 30 | 70 | 0.025 | 1800 | 30.1 | 13.1 | 111 | 2604 | 0.04 | 79 | 0.32 | 46.2 | 28 | 51 | ND*2 | 41 | ≥51.6 | 290 |
| 24 | 1250, 12 | 0.5 | 99.5 | 0.7 | 1975 | 41.2 | 12.7 | 3130 | 0.8 | 3913 | 261 | 0.21 | 65.7 | 10 | 26 | ND*2 | 28 | ≥54.1 | 541 |
| 25 | 1150, 42.5 | 0.5 | 995 | 0.007 | 2000 | 13.2 | —*1 | 31 | 17 | 1.82 | Not available | Not available | Not available | Not available | Not available | | 650 | ≥0.3 | Not measured |
| 26 | 1150, 42.5 | 2 | 98 | 0.035 | 1600 | 25.0 | —*1 | 157 | 108 | 1.45 | 79 | 0.55 | 136.4 | 52 | 41 | ND*2 | 15 | ≥44.9 | 530 |
| 27 | 1150, 42.5 | 0.5 | 99.5 | 1 | 1800 | 38.5 | 12.1 | 4480 | 17 | 264 | 128 | 0.23 | 38.6 | 1 | 22 | ND*2 | 22 | ≥55.2 | 531 |
| 28 | 1150, 42.5 | 0.5 | 99.5 | 0.003 | 1700 | 13.2 | —*1 | 13 | 24 | 0.54 | 69 | 0.42 | 69.5 | 25 | 18 | ND*2 | 120 | ≥48.0 | 340 |

*1 The XRC·FWHM was not measured because no peak appeared in the rocking curve measurement.
*2 Below the detection limit

[Evaluation]

All the alumina sintered bodies of Experimental Examples 1 to 21 had a surface with a degree of c-plane orientation of 5% or more, contained Mg and F as impurities, and had an appropriate Mg/F mass ratio and an appropriate Mg content. Furthermore, the crystal grain size, the number of pores having a diameter of 0.2 to 0.6 μm, and the pore volume fraction were also within the appropriate ranges. These alumina sintered bodies produced in Experimental Examples 1 to 21 had, at a thickness of 0.5 mm, an in-line transmittance of 60% or more at a wavelength of 450 nm to 1000 nm. That is, the in-line transmittance was high even though the degree of c-plane orientation was relatively low, and high transparency was achieved. In Experimental Examples 1 to 11 and 13 to 18, the XRC·FWHM was 15° or less. Furthermore, Experimental Examples 1 to 8, 13 to 15, 17, 18, and 20 were good in terms of high strength because the F content was 200 ppm or less and the four-point bending strength was relatively high, 350 MPa or more. Experimental Examples 9 to 12, 16, 19, and 21 were good in terms of in-line transmittance, but had a slightly low four-point bending strength of 300 MPa or less.

In the alumina sintered body of Experimental Example 22, the degree of c-plane orientation was zero. In the alumina sintered body of Experimental Example 23, the Mg/F was outside the appropriate range. In the alumina sintered body of Experimental Example 24, the Mg/F and the number of pores were outside the appropriate ranges. In the alumina sintered body of Experimental Example 25, the crystal grain size was outside the appropriate range. In the alumina sintered body of Experimental Example 26, the pore volume fraction was outside the appropriate range. In the alumina sintered bodies of Experimental Examples 27 and 28, the Mg content was outside the appropriate range. Therefore, all the alumina sintered bodies had, at a thickness of 0.5 mm, an in-line transmittance of less than 60% at a wavelength of 450 nm to 1000 nm, and high transparency was not achieved.

Experimental Examples 1 to 21 correspond to Examples of the present invention and Experimental Examples 22 to 28 correspond to Comparative Examples. The present invention is not limited to the above Experimental Examples, and various embodiments can be obviously made without departing from the technical scope of the present invention.

The present application claims priority from Japanese Patent Application No. 2015-98525 filed on May 13, 2015 and Japanese Patent Application No. 2016-11190 filed on Jan. 25, 2016, the entire contents of which are incorporated herein by reference.

What is claimed is:

1. An alumina sintered body comprising:
a surface having a degree of c-plane orientation of 5% or more, the degree of c-plane orientation being determined by a Lotgering method using an X-ray diffraction profile obtained through X-ray irradiation at 2θ=20° to 70°,
wherein the alumina sintered body contains Mg and F, a Mg/F mass ratio is 0.05 to 3500, and a Mg content is 30 to 3500 ppm by mass,
the alumina sintered body has a crystal grain size of 15 to 200 μm,
when a field of view of 370.0 μm long×372.0 μm wide is photographed with a 1000-fold magnification and the photograph is visually observed, a number of pores having a diameter of 0.2 to 0.6 μm is 250 or less, and
a volume fraction of the pores having a diameter of 0.2 to 0.6 μm in the alumina sintered body is 130 ppm by volume or less.

2. The alumina sintered body according to claim 1, wherein when a field of view of 370.0 μm long×372.0 μm wide is photographed using a scanning electron microscope with a 1000-fold magnification and the photograph is visually observed, a number of foreign substances having a diameter of 0.2 to 0.6 μm is 50 or less.

3. The alumina sintered body according to claim 1, wherein when a field of view of 1340.4 μm long×1607.0 μm wide is photographed with a 500-fold magnification and the photograph is visually observed, a number of pores having a diameter of 1 μm or more is 50 or less.

4. The alumina sintered body according to claim 1, wherein the alumina sintered body has, at a thickness of 0.5 mm, an in-line transmittance at 450 to 1000 nm of 60% or more.

5. The alumina sintered body according to claim 4, wherein the in-line transmittance is 80% or more.

6. The alumina sintered body according to claim 1, wherein a F content is 200 ppm or less.

7. The alumina sintered body according to claim 1, wherein contents of impurity elements other than Mg, C, and F are 50 ppm or less.

8. The alumina sintered body according to claim 1, wherein the Mg/F mass ratio is 0.2 to 3.5 and the Mg content is 100 to 1500 ppm by mass.

9. The alumina sintered body according to claim 1, wherein the crystal grain size is 20 to 100 μm.

10. The alumina sintered body according to claim 1, wherein an XRC full width at half maximum in rocking curve measurement is 15° or less.

11. A base substrate for an optical device, comprising the alumina sintered body according to claim 1.

* * * * *